US006488677B1

(12) United States Patent
Bowman et al.

(10) Patent No.: US 6,488,677 B1
(45) Date of Patent: Dec. 3, 2002

(54) SYSTEM FOR QUANTIFYING EDEMA

(75) Inventors: Harry Frederick Bowman, Needham, MA (US); Gregory T. Martin, Cambridge, MA (US)

(73) Assignee: Thermal Technologies, Inc., Cambridge, MA (US)

( * ) Notice: Subject to any disclaimer, the term of this patent is extended or adjusted under 35 U.S.C. 154(b) by 0 days.

(21) Appl. No.: 09/854,369

(22) Filed: May 10, 2001

(51) Int. Cl.$^7$ .................................................. A61B 5/00
(52) U.S. Cl. ........................................ 606/28; 600/549
(58) Field of Search ........................... 600/301, 547, 600/549, 587; 606/27, 28

(56) References Cited

U.S. PATENT DOCUMENTS

| | | |
|---|---|---|
| 3,750,649 A | 8/1973 | Severinghaus |
| 3,784,908 A | 1/1974 | Anderson |
| 4,059,982 A | 11/1977 | Bowman et al. |
| 4,230,126 A | 10/1980 | Elings |
| 4,257,775 A * | 3/1981 | Ladov et al. .................. 23/230 |
| 4,488,559 A * | 12/1984 | Iskander ..................... 128/653 |
| 4,676,252 A | 6/1987 | Trautman et al. |
| 4,739,711 A | 4/1988 | Manwaring |
| 4,819,648 A | 4/1989 | Ko |
| 4,841,543 A | 6/1989 | Dittmar et al. |
| 4,852,027 A | 7/1989 | Bowman et al. |
| 4,859,078 A | 8/1989 | Bowman et al. |
| 6,106,477 A | 8/2000 | Miesel et al. |
| 6,167,300 A | 12/2000 | Cherepenin et al. |

OTHER PUBLICATIONS

Thermal Properties Calculated from Measured Water Content as a Function of Depth in Porcine Skin, Burns (1986) vol. 12/ No. 8, 556–562, F. S. Knox, III, T. L. Wachtel, G. R. McCahan, and S. C. Knapp, 1986.

Thermal Conductivity and Diffusivity of Neuroblastoma Tumor, Medical Physics, vol. 5, No. 5, 418–421, Avtar S. Ahuja, Kedar N. Prasad, William R. Hendee, and Paul L. Carson, Sep./Oct. 1978.

A Convenient Method of Measuring the Thermal Conductivity of Biological Tissue, Phys. Med. Biol., vol. 36, No. 12, 1599–1605, X. G. Liang, X. S. Ge, Y. P. Zang and G. J. Wang, 1991.

Determination of the Concentrations of Binary Mixtures of Glycerine and Water by a Transient Method, Journal of Thermal Analysis, vol. 53, 855–859, L. Hu, M. Yang and C. Wang, 1998.

* cited by examiner

Primary Examiner—Max Hindenburg
Assistant Examiner—Michael Astorino
(74) Attorney, Agent, or Firm—James L. Neal (57) ABSTRACT

A system is provided for monitoring edema in tissue. Thermal energy is supplied to tissue at a site where tissue water content is to be monitored to produce in the selected tissue a thermal response as a function of an intrinsic thermal property of tissue that varies with water content. Tissue water content is determined from the thermal response, the energy supplied and the relationship between tissue water content and the thermal property.

21 Claims, 7 Drawing Sheets

SYSTEM FOR QUANTIFYING EDEMA

BACKGROUND OF THE INVENTION

Edema, the abnormal or excessive retention of fluid at a site in the body, can produce damaging stress on the body and inhibit proper functioning of organs. Edema inhibits blood flow in tissue, raises systemic blood pressure and otherwise impairs healthy body function.

Edema produces swelling which often results in a constriction of blood flow to the affected area. This can place stress on the heart, kidneys, brain, muscle tissue and other organs. Causes of edema include trauma, burns, hypersensitive reactions, thrombophlebitis and disease. Edema can even result from malnutrition, obesity and lack of exercise. In the heart, edema can produce heart failure. Cardiac edema increases the volume of the heart wall; the wall thickens and reduces the volume of the chambers of the heart. Cardiac output is reduced and the workload of the heart is increased. Head trauma often results in edema. Serious head injury is almost always associated with excessive fluid retention in brain tissue and brain swelling. As the brain swells the increase in tissue volume is confined by the rigid cranial cavity. The resulting pressure increase restricts blood supply and, if not relieved, produces brain damage. In muscle tissue edema can produce compartment syndrome. Injury can cause a volume of tissue to retain excess fluid and swell. The volume of the swelling tissue is constrained by surrounding tissue so that blood supply to the tissue is restricted.

When excessive fluid collects in tissue there is a need to mitigate the condition to avoid related adverse physiological effects and as an aid to treatment. Edema is often associated with low blood flow and its attendant problems and can affect any location or organ of the body. As water content of tissue can change from time-to-time, and sometimes rapidly, there is a need for an edema monitor which can detect tissue water content in any tissue or organ of the body and monitor it continuously.

Prior devices for measuring edema, such as those for measuring pulmonary edema, involve injection of indicator directly into the bloodstream. Catheters introduced into the circulatory system deliver the indicator and detect the response. One such device is described in U.S. Pat. No. 4,676,252 issued to Trautman et al. U.S. Pat. No. 4,819,648 to Ko discloses a device for electromagnetically sensing impedance changes in the brain to monitor brain fluid levels.

SUMMARY OF THE INVENTION

It is a purpose of this invention to provide a system to quantify the water content or condition of edema in any selected tissue or organ of the body and continuously monitor changes therein.

It is a further purpose of this invention to quantify tissue water content by modeling the relationship between tissue water content and a thermal property of tissue that varies as a function of tissue water content.

It is a purpose of this invention to provide an edema monitor in which a thermal probe is introduced into thermal communication with live tissue at a selected site and energized to transfer thermal energy to the tissue and tissue water content is determined from a thermal property of tissue which varies as a function of tissue water content.

It is an objective of this invention to assess tissue water content as a function of the power used to heat tissue at a selected site and a thermal property of tissue which varies as a function of tissue water content.

It is also an object of this invention to quantify edema in tissue as a function of the power used to heat tissue at a selected site and the thermal conductivity of tissue.

In the present invention, the monitoring of water content (edema) in live tissue is provided by detecting the thermal response of the subject tissue to the application of thermal energy and computing water content as a function of the thermal response and thermal energy or power used. Certain thermal properties of tissue vary as a function of tissue water content. For example, thermal diffusivity and thermal conductivity of the tissue increase as the water content of the tissue increases. Accordingly, the thermal response to the introduction of heat in a selected tissue sample or organ is a function of these properties. Herein, the terms tissue water content and edema are essentially synonymous, edema being a condition of abnormally high tissue water content.

A preferred embodiment, the invention includes a thermal probe which thermally communicates with tissue in contact with it and which electrically communicates with a monitor. The probe incorporates an embedded thermistor. In a minimally invasive probe, a distal thermistor is embedded in the tip of a narrow gage catheter (1-mm diameter). The catheter is inserted into tissue at a site to be examined and effects thermal contact with surrounding tissue. The thermistor, adapted for thermal contact with the tissue, is heated to a small increment above the tissue temperature baseline. (For example the temperature of the thermistor surface may be elevated to a predetermined temperature approximately 2° C. above the tissue temperature baseline.) A second or proximal thermistor may be embedded in the probe for monitoring tissue baseline temperature and compensating for baseline temperature fluctuations. The distal thermistor is heated at intervals by power source within a control circuit. The power used to elevate the temperature in an interval is indicative of a value of the selected thermal characteristic, for example, thermal conductivity and/or thermal diffusivity, in tissue at the location of the thermistor. The sensed temperature results in a signal from the power source functionally related to the thermal response in the tissue to the application of heat, which signal is used to calculate a value indicative of tissue water content. The following example is based on thermal conductivity.

When the thermistor is in thermal contact with live tissue at a site where water content is to be assessed, the power dissipated by the heated thermistor (typically within the range of 0.005–0.01 W) provides a measure of the ability of the tissue to carry heat by both conduction in the tissue and convection due to tissue blood flow. In operation, the thermistor is energized and a thermal field propagates into tissue contacting and surrounding the thermistor. The initial propagation of the field is due substantially to inherent tissue conductivity (thermal conductance). Subsequent propagation of the field is affected more by tissue convection (blood flow or perfusion). A monitor or data processor controls the probe, records the data and distinguishes between the effect of the inherent thermal conductivity characteristic of the tissue and convective heat transfer due to tissue blood flow. The inherent or intrinsic thermal conductivity of the tissue at the site of the thermistor is determined from the initial rate of propagation of the thermal field in the tissue, separated from the effects of convective heat transfer.

A data processing technique by which the thermal conductive and convective effects of the heated thermistor are distinguished and separated will now be discussed. Measurements are made under effectively transient conditions, i.e., at times which are short relative to the time required for the system to reach steady state. Accordingly, the temperature change produced in the tissue is permitted to vary in any arbitrarily selected manner with time. The power required to heat the tissue and the resulting temperature change are recorded. An intrinsic thermal conductivity value is calculated using data obtained at an initial time period. The conductivity value is used to assess the fluid content (or edema) of tissue at the site of the probe. The water content of the tissue is computed as a function of the intrinsic thermal conductivity of the tissue and data derived by using a model of the relationship of intrinsic tissue conductivity values to tissue water content values.

As is often the case in monitoring procedures, there is some margin of error that must be held within a range deemed appropriate for acceptable or optimum operation. When direct computation of conductivity (or other thermal property) does not lead to an acceptably accurate calculation of water content, an iterative process may be used to optimize the accuracy of the water content calculation. For example, computation can be based on a thermal model requiring a series of heating cycles with measurements at two or more selected times within each cycle. These measurements occur during a temperature change cycle in which the temperature of tissue at the selected site is raised from a first unperturbed value to a second value and relaxed back to an unperturbed value. A thermal model and related mathematical equations are described in U.S. Pat. No. 4,852,027 to Bowman et al. When data used to assess the thermal conductivity of tissue includes measurements made at least two selected time periods in an overall temperature changing cycle, data processing occurs in an interactive or iterative operation so as to converge relatively rapidly to a final solution for conductivity of tissue at the site of the probe. In one embodiment, the thermistor is energized to heat the tissue at the selected site from an unperturbed temperature value to a second higher temperature value and then permitted to decay, i.e. to cool, to an unperturbed value. Power is applied to energize the thermistor in any appropriate manner that produces an arbitrarily selected change as a function of time in the volume mean temperature of the tissue surrounding the thermistor. Measurements are made in at least two selected time periods during the heating and cooling cycle. The effects of the flow in the tissue (perfusion) on the measurements involved are least (substantially negligible) during the initial stage of the heating cycle and greater during the later portion of the cycle. Particularly, the effects of flow are greater during the cooling portion of the cycle than during the heating portion.

In the iterative computation, the temperature of the thermistor is caused to rise to initiate each heating cycle and relax at the end of each cycle. An initial determination of a value for intrinsic thermal conductivity (or thermal diffusivity), is calculated during a first time period in the initial and each subsequent heating cycle. This first time period calculation is made at the initial stage of each heating cycle. A calculation of the convective heat transfer effect in the tissue due to perfusion of the tissue is separately calculated at a second time period, later in the heating cycle, using the conductivity value obtained in the initial time period and perfusion data obtained at the second time period, the effects of convective heat transfer during the second time period being greater than the convective heat transfer effects during the first time period. The perfusion value obtained at the second time period is used to recompute a second, more accurate value of thermal conductivity in the first time period. The process can be repeated as many times as necessary. In each calculation of perfusion the value of conductivity obtained in the prior calculation is used. Similarly, in each successive computation of thermal conductivity the prior value of perfusion is used. The iterative process will lead to convergence wherein the same value of thermal conductivity is obtained in successive calculations. This value of conductivity can be used to compute the fluid content of tissue at the location of the probe.

The calculation of edema in the above described embodiment thus takes into account the effective thermal conductivity of the subject tissue, that being the convective heat transfer effect produced by tissue perfusion plus the intrinsic thermal conduction of the tissue, and separates the convective heat transfer effect (perfusion) from the intrinsic thermal conductivity. (Similarly, effective thermal diffusivity is the intrinsic thermal diffusivity of the tissue plus the perfusion related diffusivity effects.)

DETAILED DESCRIPTION OF THE DRAWINGS

Figure 1:
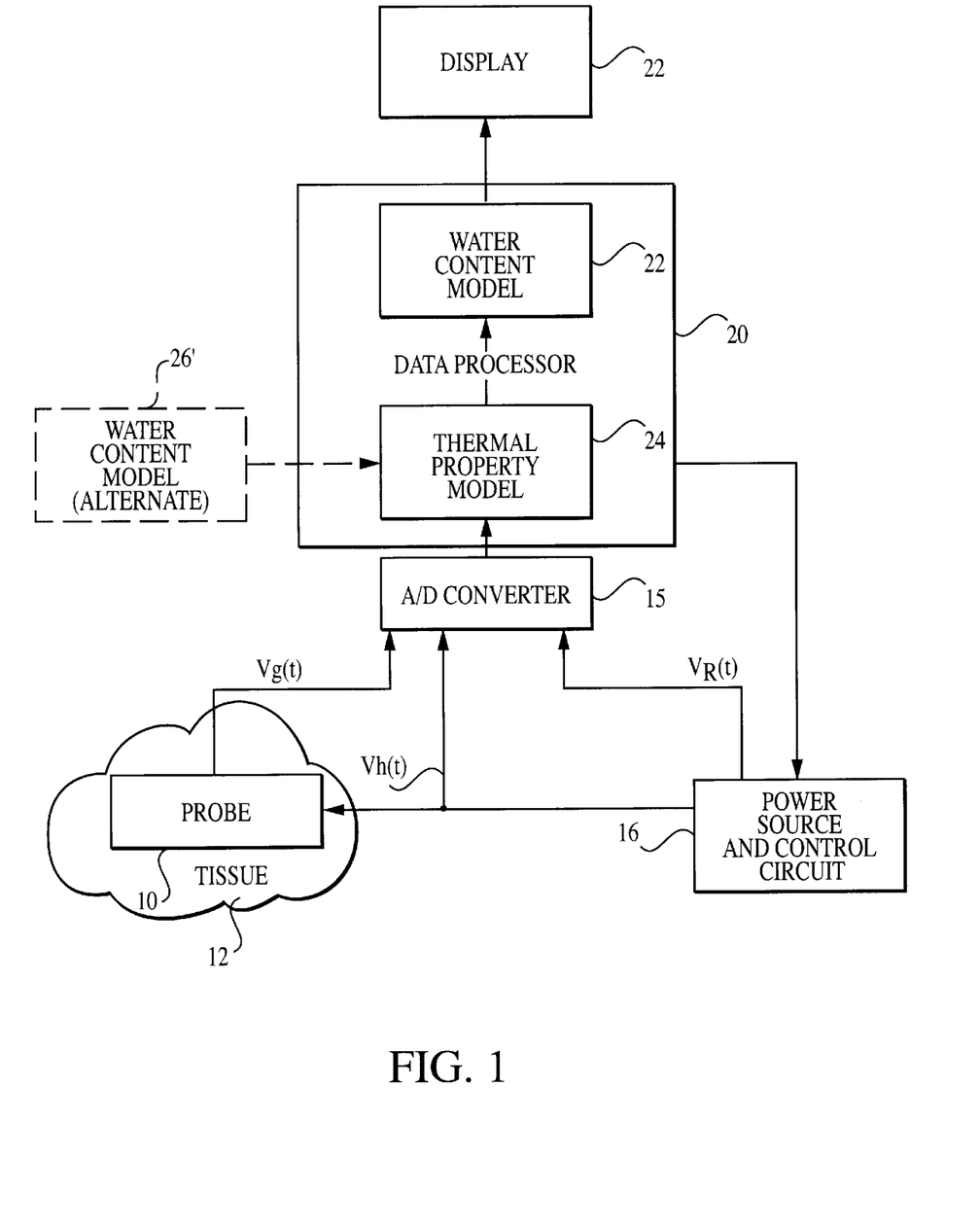
FIG. 1 is a block diagram of a system according to one embodiment of the invention.
Figure 2A:
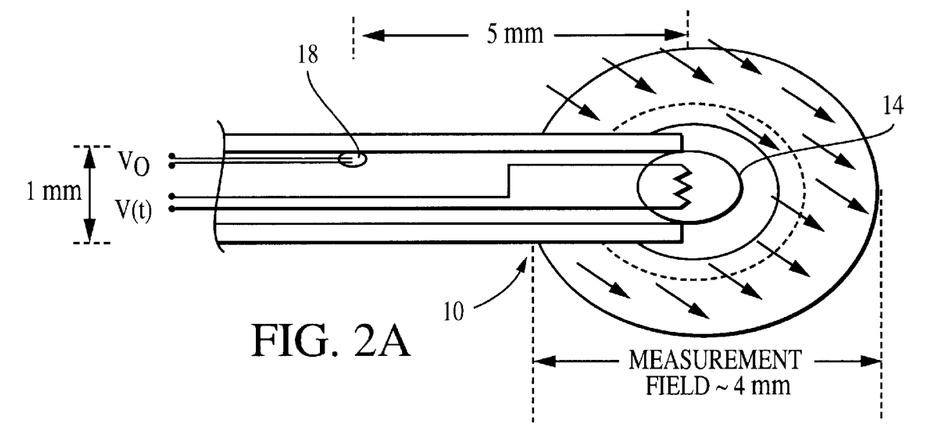
FIG. 2A illustrates one example of a probe useful in connection with an embodiment of this invention diagrammed in FIG. 1.
Figure 2B:
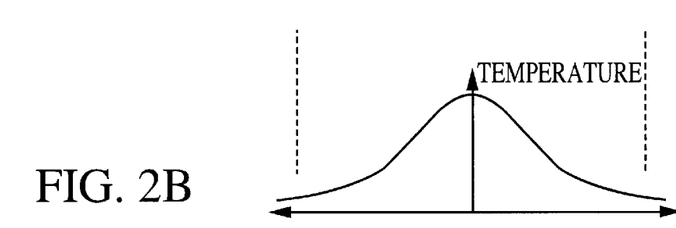
FIG. 2B illustrates a typical pattern of heat distribution in tissue produced by the heated probe of FIG. 2A.

A system such as that shown in FIG. 1 and, for example, a probe of the type shown in FIG. 2A can specifically implement the techniques of the invention. As shown, a probe 10 is immersed in tissue 12. A self-heating distal thermistor 14 mounted on a catheter 11 is heated by power from an electrical power source and control circuit 16. In FIG. 1 the heater voltage supplied via the power source and control circuit 16 is indicated as $V_h(t)$. The thermistor 14 is energized to heat a surrounding volume of tissue 12. The mean temperature of the thermistor 14 is rapidly raised to a predetermined level above its initial equilibrium temperature, or above the baseline temperature of tissue 12, by the power source and control circuit16. A typical heat distribution pattern in tissue 12 is illustrated in FIG. 2B. The maximum temperature occurs at the center of the thermistor bead and decreases in all directions therefrom to the reference temperature; that is, it decreases to the baseline temperature of the unperturbed tissue surrounding the site of the thermistor. The volume of tissue surrounding the thermistor 14 in which the temperature of the tissue is elevated to any substantial extent by the heated thermistor is referred to as the measurement field.

The rate at which heat is transferred from the thermistor 14 is a function of the effective thermal conductivity of the tissue 12. The power used or dissipated in the thermistor to maintain a predetermined elevated temperature level thus is also a function of the effective thermal conductivity of the surrounding tissue. The effective thermal conductivity of living tissue has two principal components, intrinsic thermal conductivity of the tissue and tissue perfusion (i.e.: the effect of convection in the tissue). Intrinsic thermal conductivity of tissue is a function of tissue water content. Therefore the rate of heat transfer from the thermistor 14 and in tissue 12 is also a function of tissue water content. The voltage $V_h(t)$ across the thermistor 14 (an electrically resistive thermistor bead which is heated in an active mode and unheated in a sense mode) provides a parameter from which a determination of the effective thermal conductivity is made. In the data processor 20 the thermal effect of intrinsic thermal conductivity and the thermal effect of perfusion are separated and the intrinsic thermal conductivity value is used in the calculation of tissue water content The signal $V_h(t)$ from the power source and control circuit 16 is indicative of the power or thermal energy supplied by the control circuit 16 to the thermistor 14, the value of which is also a function of the thermal response in the tissue resulting from the application of heat. The signal $V_h(t)$, functionally related to effective thermal conductivity of tissue 12, is supplied in digital form via a suitable analog-to-digital converter 15 to a digital data processor 20 which computes the intrinsic thermal conductivity. A proximal thermistor 18, located on probe 10 to be outside the thermal range or measurement field of thermistor 14, monitors the baseline temperature and provides a signal $V_s(t)$ which adjusts for baseline temperature shifts. The proximal thermistor 18 is an option used where baseline temperature shifts are (or are expected to be) substantial enough to interfere with effective monitoring. In stable thermal environments the compensation provided by thermistor 18 is not required.

The data processor 20 processes power related signals from the control circuit 16 and baseline signals from the thermistor 18 (if used) and provides to a display device 22 a signal the value of which is indicative of tissue water content. A display device then displays the assessment of tissue water content. More particularly, the thermal property model 24 (which may be an algorithm forming part of data processor 20) communicates with power source 16, water content model 26 (which also may be an algorithm forming part of data processor 20) and probe 10. The thermal property model 24 determines the intrinsic thermal conductivity (k) as a function of the power supplied to the thermistor 14 (via the signal $V_h(t)$ provided by control circuit 16) and, in an embodiment where baseline adjustment is required, a baseline signal from thermistor 18. Drawing on the water content model 26 and the thermal property model 24, the data processor 20 computes the water content of tissue 12.

In the embodiment shown in FIG. 1, an intrinsic thermal conductivity data signal is provided to the water content model 26 from the thermal property model 24. The water content model 26 relates the conductivity value to a corresponding value for tissue water content. The tissue water content or edema value provided by the model 26 is communicated to the display device 22 for appropriate display. Tissue water content or edema is determined by water content model 26 which correlates the conductivity signal provided by the thermal property model 24 with a corresponding tissue water content value. The thermal property model 24 and the water content model 26 will be discussed further below.

The example given is directed to the use of an invasive probe 10 having thereon a thermistor 14 to which power is applied to heat the thermistor and, accordingly, to heat the tissue surrounding it. However, the invention is not so limited. For example, rather than applying heat to the tissue in an internal or invasive sense by applying power to a probe immersed in the tissue, heat can be applied non-invasively to the tissue from an external heat source. Examples of probes that are adapted for non-invasive use are shown in U.S. Pat. No. 4,859,078 to Bowman et al. and U.S. Pat. No. 4,841,543 to Dittmar et al. Probes such as these can be used on the skin surface or, during surgery, on the surface of an internal organ without penetrating the skin or organ with a probe. The volume of tissue within the measurement field is that volume of tissue which is heated above the tissue baseline temperature.

Figure 3:
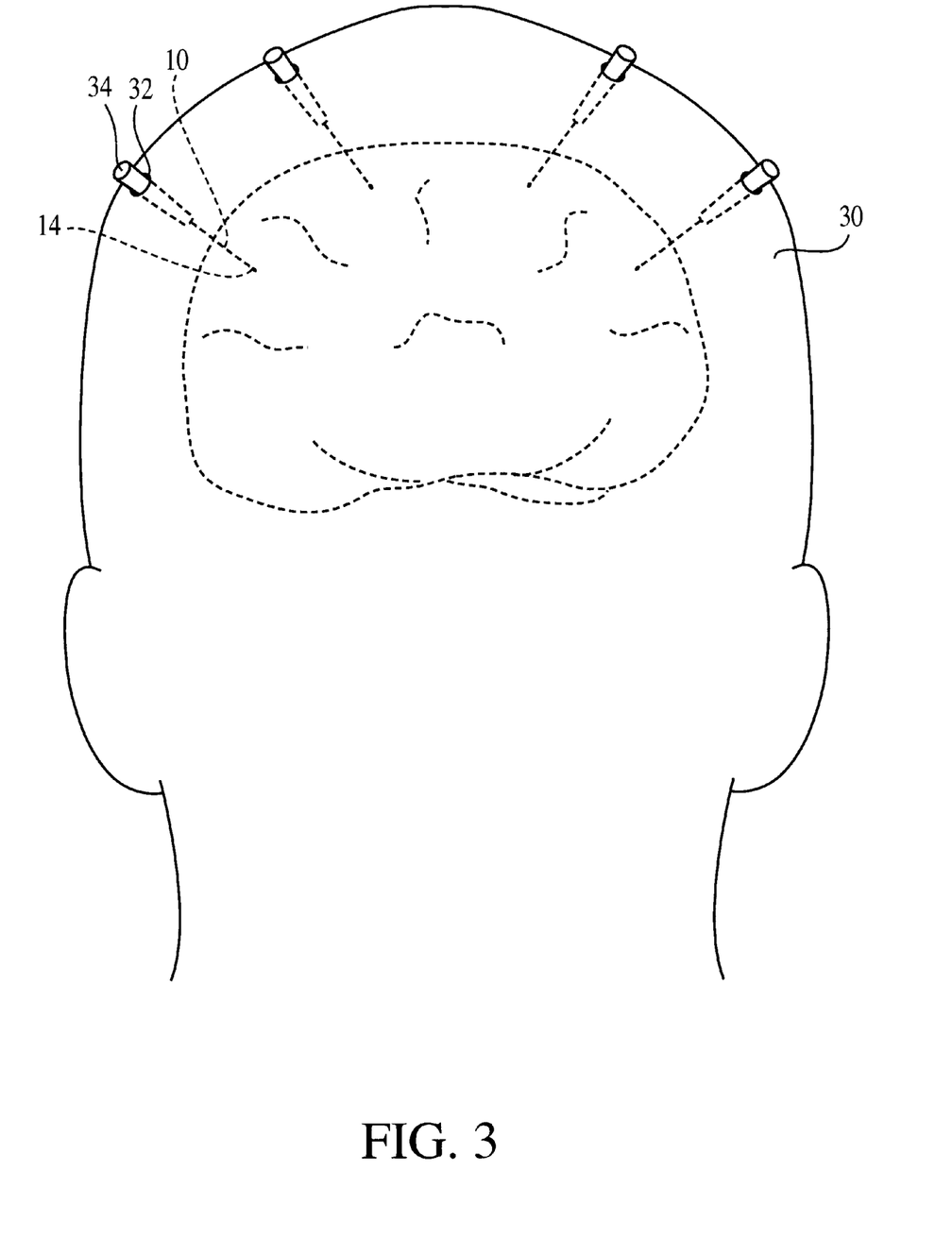
FIG. 3 is a schematic view of the invention as applied in monitoring brain tissue.

A representation of the system of this invention for monitoring edema in the brain is illustrated schematically in FIG. 3. In some cases of head trauma and some surgeries, one or more openings or burr holes 32 are formed in the skull 30 and fitted with hollow bolts 34 to provide access to the brain cavity. The hollow bolts can serve as an access to the brain for introduction of the probe 10. The probe 10 is passed through the hollow bolt 34 to imbed the distal thermistor 14 in brain tissue. In embodiments with a baseline monitoring proximal thermistor 18, the probe 10 is positioned so the thermistor 18 is also imbedded in brain tissue. Brain edema is monitored during surgery and can be monitored following surgery. One use for the tissue water content data is to identify a condition of edema associated with swelling of the brain sufficient to cause constriction of blood flow, so appropriate treatments or surgical interventions can be made. In other surgeries, such as heart surgery, the probe 10 or a non-invasive probe may be applied to the heart or to surrounding tissue to assess tissue fluid retention at those locations.

Figure 4:
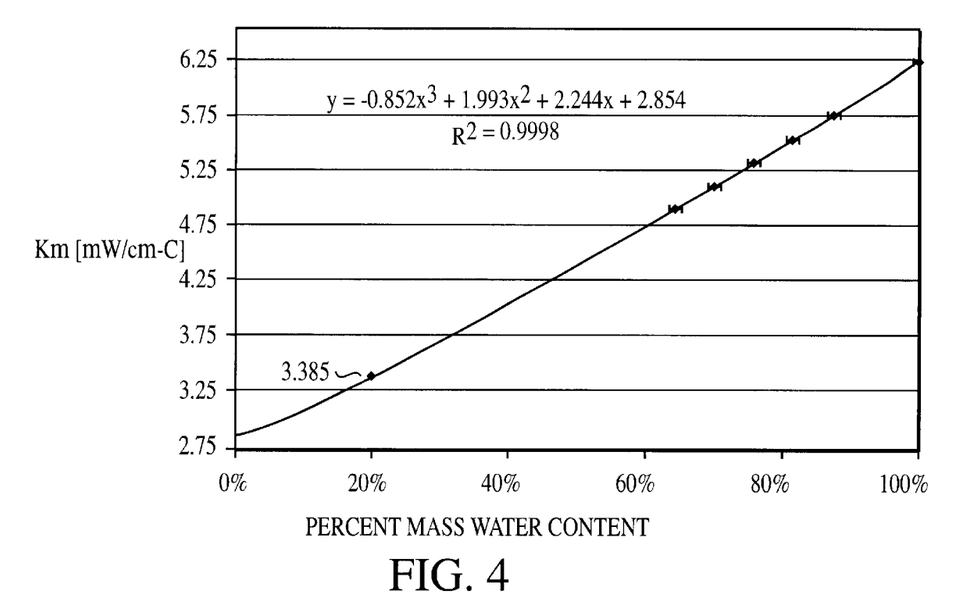
FIG. 4 illustrates an empirical water content model as a curve of conductivity versus percent mass water content.

The tissue water content model 26 will now be described. The tissue water content model may be formulated to model a thermal property of tissue that varies in a known way with tissue water content. For example, values for rates at which heat may be transferred in tissue can be related by the model with corresponding tissue water content values. The relationship established by the model and the power supplied to heat a volume of tissue at a selected site can be used to quantify water content of tissue at the site. One such model based on the thermal conductivity of tissue is an empirical model that correlates possible or probable intrinsic thermal conductivity values with corresponding values of tissue water content. This model is based upon the conductivity of the three major components constituting tissue, water, fat and protein. The thermal conductivity of water is 6.23 mW/cm-°C. and the thermal conductivity of both fat and protein approximate 2.00 mW/cm-°C. The values for fat and protein are sufficiently close to each other and sufficiently distinct from that of water that an effective model can be based either on an assumed approximate value (for example 2.0) for both fat and protein or on individual values for fat and protein. An empirical model of tissue conductivity at various percentages of water content can be formulated using a water-glycerol mixture with the glycerol (having a thermal conductivity of 2.85 mW/cm-°C. at 37° C.) being the model for fat and protein. Measurements taken using a water-glycerol mixture yielded the curve illustrated by FIG. 4. In the range of 60% to 100% water content, which is the range in which most applications of the invention fall, the data points fall substantially in a straight line indicating water content to have substantially a linear relationship with conductivity. A line that fits the data points can be expressed as:

$$y=3.802x+2.445 \quad (1)$$

where "y" represents thermal conductivity and "x" represents percent mass water content. Below 60% water content, the data points measured in the water-glycerol mixture were not linear. A curve that fits the data over the full 0%–100% range of water content can be expressed as:

$$y=-0.852x^3+1.993x^2+2.2436x+2.854 \quad (2)$$

where "y" represents thermal conductivity and "x" represents percent mass water content.

An empirical model can also be based on actual tissue measurements when there is independent confirmation of the water, fat and protein content of the tissue samples in which thermal conductivity data are taken.

Figure 5:
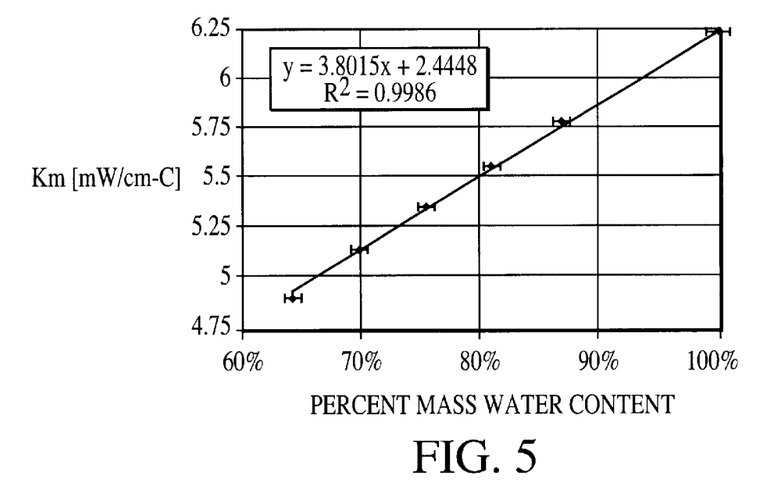
FIG. 5 illustrates a theoretical water content model.

Additionally, the model can be based on theoretical values for thermal conductivity of fat, protein and water. An example is shown by FIG. 5, where there is essentially a straight-line relationship between thermal conductivity and percent mass water content. The relationship can be expressed as:

$$y=ax^3+bx^2+cx+d; \quad (3)$$

where "y" represents thermal conductivity, "x" represents percent mass water content and a, b, c, and d are constants. This expression is similar in form to Expression No. 2, above.

The above referenced models for intrinsic thermal conductivity of tissue are based on the principle that the conductivity of a volume of tissue is a function of the conductivity of each constituent component, weighted by its mass fraction. That is:

$$m_t=m_h+m_f+m_p. \quad (4)$$

Where: $m_t$ is the mass of the tissue; $m_h$ is the mass of the water component; $m_f$ is the mass of the fat component and $m_p$ is the mass of the protein component.

Dividing Equation (4) by the mass of tissue ($m_t$) to obtain the mass fraction, the result is:

$$1=\gamma+\beta+\theta \quad (5)$$

Where: $\beta=m_h/m_t$=the mass fraction of water in the tissue; $\beta=m_f/m_t$=the mass fraction of fat in the tissue; and $\theta=m_p/m_t$=the mass fraction of protein in the tissue.

Therefore the conductivity of tissue can be expressed in terms of mass fractions as:

$$k_t=\gamma k_h+\beta k_f+\theta k_p \quad (6)$$

Where: $k_t$ is the conductivity of tissue; $k_h$ is the conductivity of water in the tissue, $k_f$ is the conductivity of fat in the tissue and $k_p$ is the conductivity of protein in the tissue.

Similarly, other thermal properties of tissue (such as diffusivity) can be expressed in terms of mass fractions as:

$$\alpha_t=\gamma\alpha_h+\beta\alpha_f+\theta\alpha_p \quad (7)$$

Where $\alpha t$ is the thermal property (such as diffusivity) of tissue, $\alpha_h$ is the thermal property of water in the tissue, $\alpha_f$ is the thermal property of fat in the tissue and $\alpha_p$ is the thermal property of protein in the tissue.

In addition, one tissue water content model may be formulated from another when the relationship between them is known. For example, in the case of thermal diffusivity, the relationship between conductivity (k) and diffusivity ($\alpha$) is expressed as:

$$\alpha=k/pc \quad (8)$$

Where p and c are, respectively, density and heat capacity. Accordingly a water content model for diffusivity can be calculated readily from the conductivity model.

Figure 6:
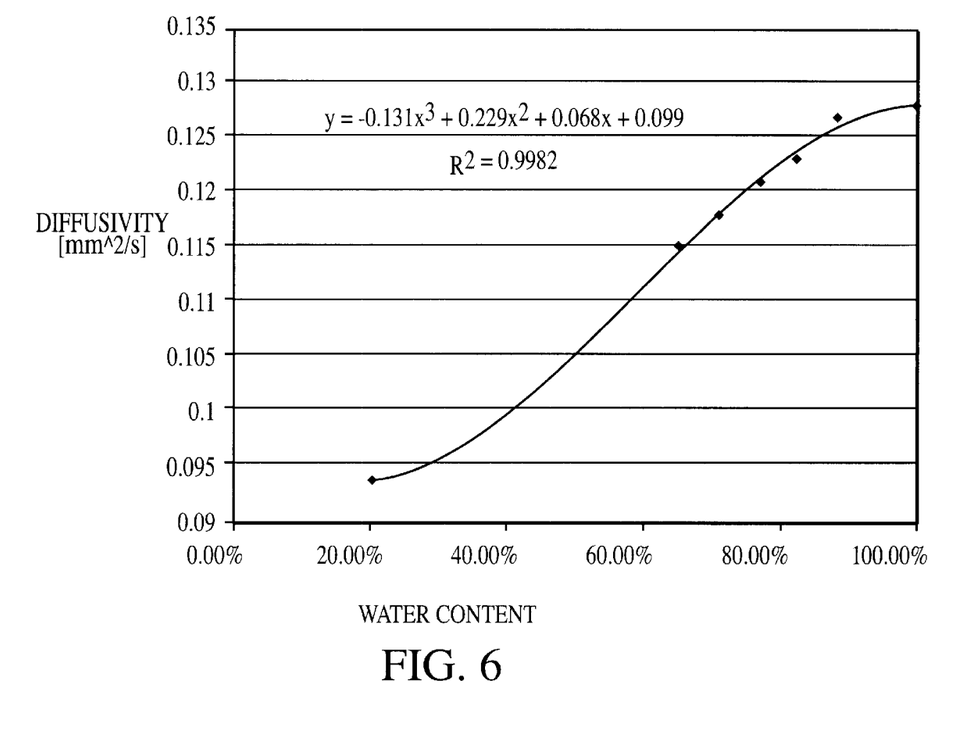
FIG. 6 illustrates an empirical water content model as a curve of thermal diffusivity versus percent mass water content.

A model for diffusivity can also be empirically derived, for example, with the same water-glycerol mixture described in connection with empirical development of the conductivity model. One such model is illustrated by FIG. 6. A curve that fits the data points of FIG. 6 can be expressed as:

$$y=-0.131x^3+0.229x^2-0.068x+0.99. \quad (9)$$

where "y" represents thermal conductivity and "x" represents percent mass water content.

Since the water content of tissue changes, this change is reflected in a corresponding change in the intrinsic value of the thermal property such as conductivity and diffusivity. During injury to tissue, for example, water content will typically increase resulting in the condition of edema. According to this invention, a measure of at least one of the water-dependent thermal properties of tissue, for example, intrinsic thermal conductivity, in an area of injury is made and used to quantify the tissue water content (i.e.: to quantify edema). The data processor 20 is programmed with a model of the relationship of conductivity and tissue water content, such as one of those referenced above. The system processes thermal conductivity data in accordance with a tissue water content model as described above to quantify the percent mass water content of tissue (or edema) and provide an appropriate display.

The water content model 26 may function as a look-up reference wherein for any known value of a tissue thermal property such as conductivity or diffusivity, a corresponding or related value for tissue water content is provided.

It will be appreciated that, in alternate data processing techniques, tissue water content can be computed directly from the primary data, without actually computing a value signal for conductivity. For example, the data processor 20 can be caused to compute water content in response to data supplied via circuit 16, input from a model of tissue water content (as illustrated by alternate water content model 26' in FIG. 1) and data from the probe 10. Alternate model 26' acts as a look-up reference that correlates tissue thermal property values, such as conductivity and diffusivity, to water content. The alternate model 26' provides to the data processor 20 an input of the correlated water content values and the data processor calculates the water content of the subject tissue as a function of the three inputs: correlated data input from the alternate model 26'; the signal from the control circuit 16 functionally related to the power required to heat the thermistor 14; and the baseline signal from probe 10.

The above-described techniques calculate tissue water content based on measurements of a thermal property variable with water content (e.g.: thermal conductivity or thermal diffusivity) in the selected tissue. To monitor continuously, the values for edema calculated as described are recalculated in rapid succession. The thermistor 14 is cyclically energized and deenergized to produce repetitive heating cycles and edema is recalculated in each energizing cycle, during each rise and fall of the temperature of the thermistor. By the described techniques of this invention, an updated edema value can be obtained, for example, every three to six minutes.

A description of thermal property model 24 and mathematics for a method for determining effective thermal conductivity, thermal diffusivity and intrinsic thermal conductivity are described in the above referenced U.S. patents to Bowman et al. U.S. Pat. Nos. 4,059,982 and 4,852,027. As taught there, various heating protocols can be used to heat the thermistor. The thermistor 14 can be heated to a constant or predetermined temperature or thermistor temperature can be measured during heating at a constant or predetermined power or other heating protocols can be used. In all protocols, procedures using the same principles are used to analyze data. Power used to heat the thermistor and the temperature rise of the thermistor are functional inputs to the calculation of tissue water content and, in calculating water content, one of the values is predetermined. Two heating protocols will be described, one in connection with FIG. 7 and a second in connection with FIGS. 8, 9A and 9B.

Figure 7:
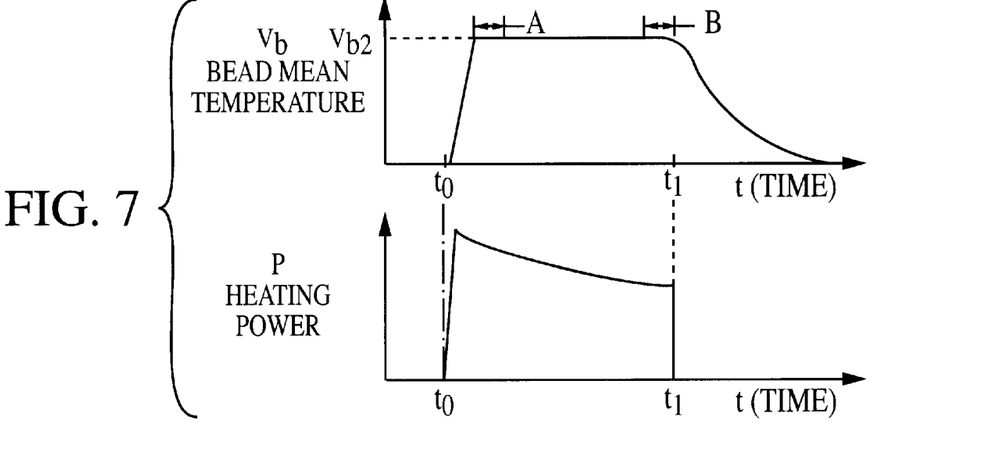
FIG. 7 depicts curves of thermistor temperature and power as a function of time in accordance with an embodiment of the invention.

In FIG. 7, graphical representations are presented of the mean bead temperature $V_b$ and of the heating power P, both as functions of time. In the particular procedure illustrated, power P is applied at to in a manner such that the thermistor bead temperature $V_b$ rapidly rises to a selected level $V_b2$ to heat a volume of tissue and is maintained at that level for a selected time period (until time $t_i$, for example) at which time the power is reduced to zero (shut-off) and the temperature $V_b$ falls to baseline temperature in a general manner as shown, completing one energizing and deenergizing cycle.

Approximation algorithms, as discussed below, can be used with data derived from measurements taken at different times during the overall heating/cooling cycle as, for example, early in the heating portion thereof at the time range or time window, illustrated by "A" in FIG. 7 and later in the heating portion at "B".

Data taken during time window "A" are dominated by tissue conduction (i.e.: conductivity) and the effects of the flow (perfusion) in the tissue are relatively low. Data taken during the time window "B", occurring later in time as heating continues, are influenced to a greater extent by perfusion, (i.e.; the effects of flow in the tissue are greater than at time window "A".)

Figure 10:
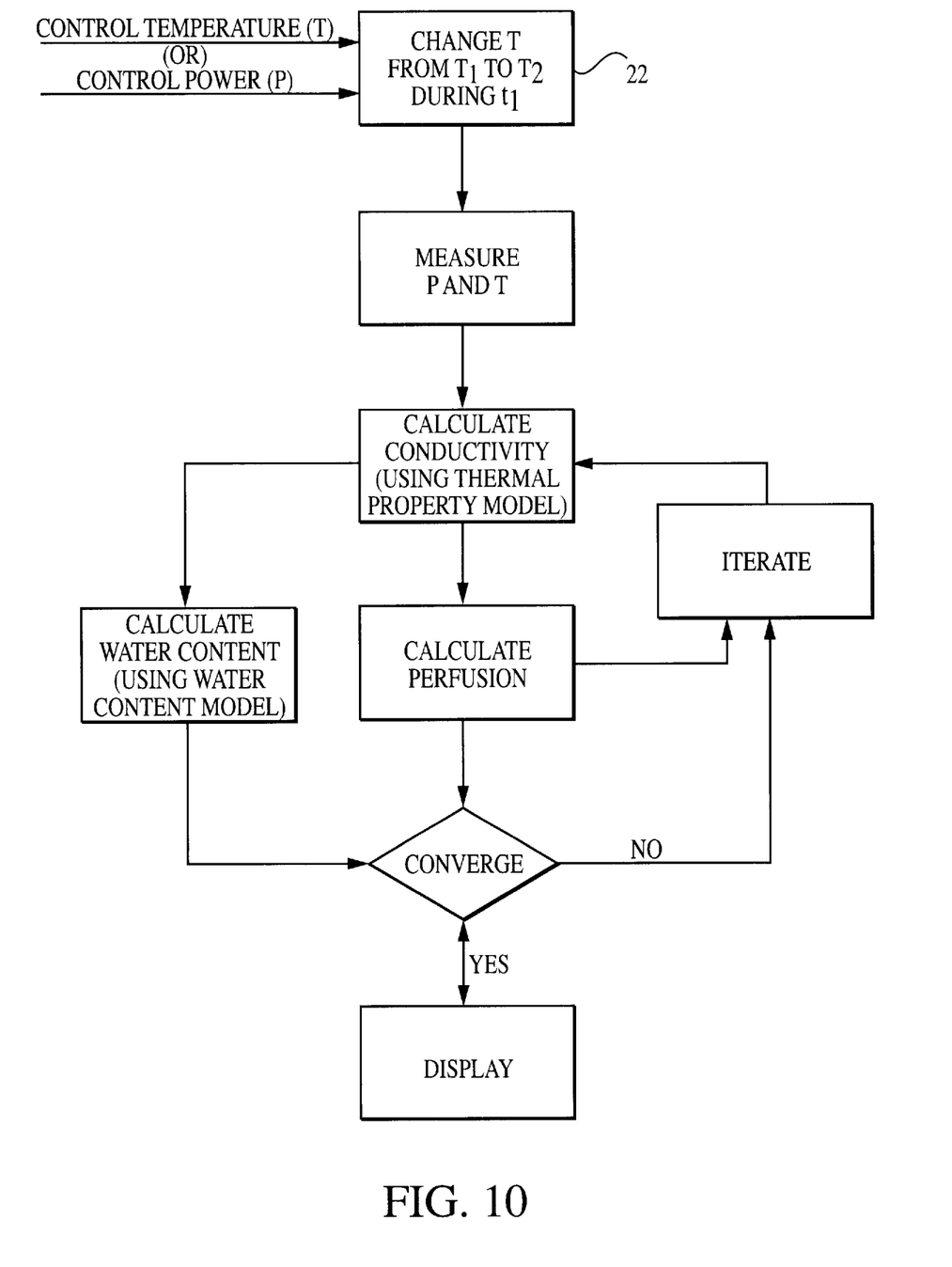
FIG. 10 is a flow chart illustrating an exemplary embodiment of the invention.

One exemplary data analysis algorithm usable at time windows "A" and "B" is illustrated by the flow chart of FIG. 10. As stated, the effects of the flow of the medium during the time window "B" are greater than during time window "A" (FIG. 7). Calculations with respect to time windows "A", and "B" can be made as follows: (1) Cause the temperature of the thermistor to change from a first temperature ($T_1$) to a second temperature ($T_2$) to initiate a thermal cycle while controlling in a predetermined manner either the temperature or the power required to effect the temperature change; (2) cause the temperature to relax from the second temperature to a final temperature ($T_f$) at the end of a heating cycle; (3) measure temperature and power; (4) calculate a value of the intrinsic thermal conductivity and/or diffusivity during time window "A"; (5) assuming a value of zero for perfusion; calculate a tissue water content (edema) using the values(s) from step (4) and the water content model; and (6) display the calculated tissue water content value.

Alternately, if a smaller margin of error is required than that obtained above in step (5), iterative calculations are performed following step (4) as follows: (7) using the calculated values of intrinsic thermal conductivity and/or diffusivity from step (4), calculate a value for perfusion during time window "B"; (8) using the calculations of the thermal conductivity and/or diffusivity as calculated during time window "A" and the perfusion value as calculated during time window "B" recalculate the thermal conductivity and/or diffusivity during time window "A" (9) using such recalculations for intrinsic thermal conductivity and/or diffusivity, recalculate the value for perfusion during time window "B"; (10) using such recalculated perfusion and recalculated values for intrinsic thermal conductivity and/or diffusivity recalculate again thermal conductivity and/or diffusivity; (11) repeat steps (9) and (10) until convergence to substantially non-changing thermal conductivity and/or diffusivity value(s) is achieved; (12) calculate to quantify tissue water content (edema) using the values(s) from step (11) and the water content model; and (13) display the calculated tissue water content.

Figure 11:
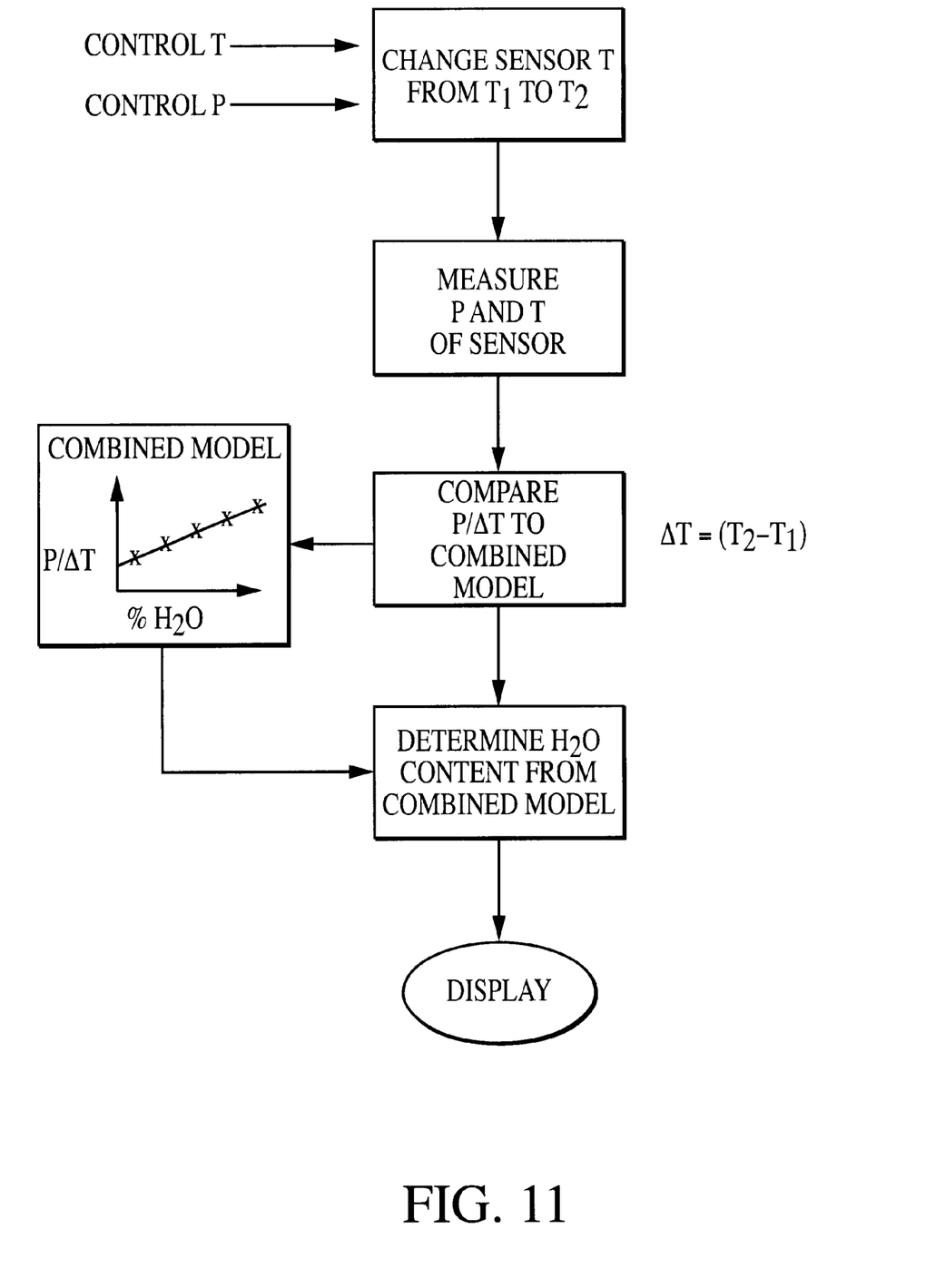
FIG. 11 is a flow chart illustrating another exemplary embodiment of the invention.

FIG. 11 illustrates a further embodiment in which water content is determined from various parameters affected by the conductivity or other thermal property of tissue without a calculation of the thermal property value. Temperature, power and a model that relates them both (P/ΔT) to tissue water content (% $H_2O$) are used in the direct calculation of water content. The model may be empirically or theoretically based. The steps are: (1) cause the temperature of the thermistor to change from a first temperature ($T_1$) to a second temperature ($T_2$) to initiate a thermal cycle while controlling either the temperature or the power required to effect the temperature change; (2) cause the temperature to relax from the second temperature to a final temperature ($T_f$) at the end of a heating cycle; (3) measure temperature (T) and power (P); (4) Determine the ratio of power to the change in temperature (P/ΔT); (5) using the combined model determine a water content value corresponding to the value of P/ΔT resulting from step (4); and (6) display the water content value.

Figure 8:
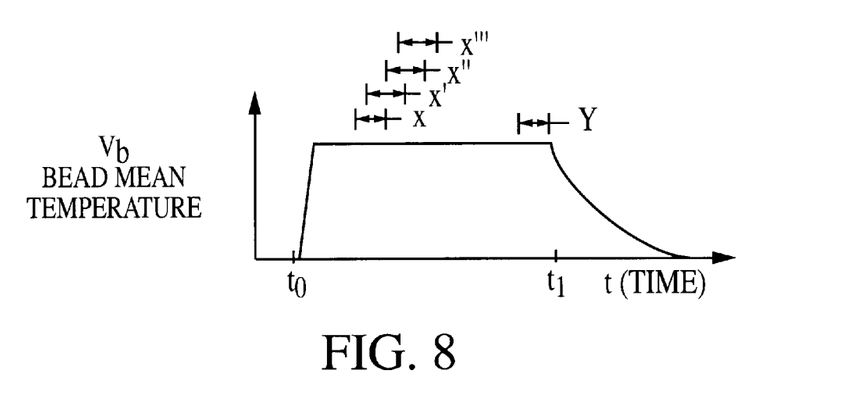
FIG. 8 shows curves of thermistor temperature as a function of time in accordance with another embodiment of the invention.
Figure 9A:
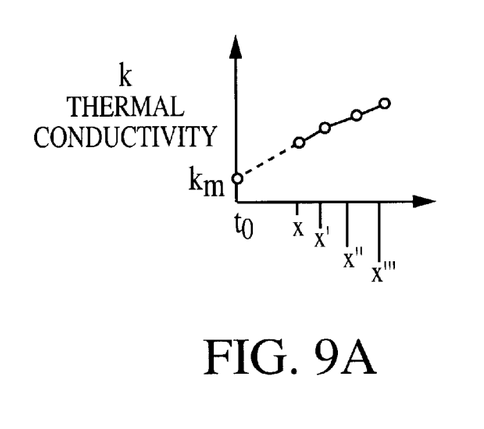
FIG. 9A is an extrapolated curve of thermal conductivity with reference to the embodiment of the invention referred to in connection with FIG. 8.
Figure 9B:
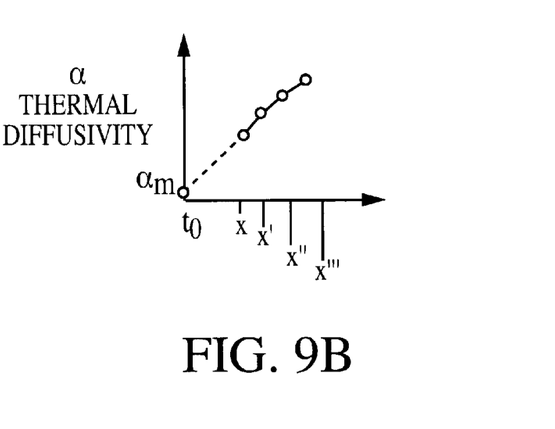
FIG. 9B is an extrapolated curve of thermal diffusivity with reference to the embodiment of the invention referred to in connection with FIG. 8.

Another exemplary alternative algorithm will be described in connection with FIGS. 8, 9A and 9B. FIG. 8 illustrates an energizing cycle similar to that shown in FIG. 7. FIGS. 9A and 9B illustrate, respectively, data extrapolations for thermal conductivity and thermal diffusivity. The calculation of edema consists of the following steps: (1) calculate a plurality of effective thermal conductivity and/or thermal diffusivity values during a plurality of time windows $X_I$ where $X_I$ is X, $X_I$, $X_{II}$, etc, with an assumed perfusion value of zero; and (2) extrapolate the thermal conductivity and diffusivity values obtained in step (1), above to time to, i.e., to the instant of time at which heating begins, to obtain values for intrinsic thermal conductivity and/or intrinsic thermal diffusivity. (See FIGS. 9A and 9B.) (The points X, $X_I$, $X_{II}$, etc. are selected at the same normalized position within each window, e.g. the middle or the end of each window). The extrapolated values will be the nonperfused, intrinsic thermal conductivity (k) value and the nonperfused, intrinsic thermal diffusivity (α) value; (3) calculate a tissue water content (edema) using the values(s) from step (2); and (4) display the calculated tissue water content value. A value for tissue water content (edema) with no substantial margin of error can be obtained by continuing the calculation process according to the following steps: (5) use extrapolated values of intrinsic thermal conductivity and diffusivity from step (2) above to calculate the perfusion at a selected time during which a perfusion effect occurs, e.g. time window "Y" (FIG. 8); (6) recalculate the intrinsic thermal conductivity and diffusivity at said plurality of time windows $X_I$ using the calculated perfusion value for the selected time window "Y"; (7) extrapolate the thermal conductivity and diffusivity values obtained in step (6) to time to; and (8) repeat steps (6) and (7) until intrinsic thermal conductivity and thermal diffusivity values converge to substantially non-changing values; (9) calculate tissue water content (edema) using the values(s) from step (8); and (10) display the calculated tissue water content value.

While the above illustrative embodiments discuss procedures in which the temperature is raised to and maintained at a higher level for a finite time period, this analysis technique may also be applied to measurements obtained when the temperature is raised to an appropriate level and immediately allowed to relax to an unperturbed value, the most crucial time for the thermal property measurements being the time or instant when the heating cycle is begun.

The invention is not to be deemed as limited to the particular embodiments described above, except as defined by the appended claims.

What is claimed is:

1. A method for quantifying water content of living tissue comprising the steps of:

contacting tissue with a thermistor at a site where tissue water content is to be quantified;

energizing the thermistor to cause the temperature of a volume of tissue to rise; and calculating tissue water content of said volume of tissue as a function of the power used to heat said thermistor and the temperature rise of said thermistor, at least one of which is controlled in a predetermined manner, and a value obtained from a model relating tissue conductivity to tissue water content.

2. A method according to claim 1 wherein:

said energizing step comprises the step of energizing the thermistor cyclically to cause the temperature of a volume of tissue to rise and fall cyclically; and said calculating step comprises the step of calculating tissue water content of said volume of tissue in each energizing cycle as a function of the power used to heat said thermistor in each energizing cycle and the temperature rise of said thermistor in each energizing cycle, at least one of which is predetermined, and a value obtained from a look-up reference relating tissue conductivity to tissue water content.

3. A method for quantifying water content in living tissue comprising the steps of:

heating a volume of tissue to produce therein a thermal response functionally related to the thermal conductivity of the tissue;

producing a signal functionally related to said thermal response and the thermal energy supplied in said heating step;

calculating the intrinsic thermal conductivity of the volume of tissue in a first time interval during said heating step;

calculating the perfusion of the volume of tissue in a subsequent time interval during said heating step using the calculated value of intrinsic thermal conductivity;

recalculating intrinsic thermal conductivity in said first time interval using the calculated value of perfusion;

recalculating values for perfusion and intrinsic thermal conductivity, in alternating fashion, until the recalculated values of intrinsic thermal conductivity converge to a substantially unchanging value, using in each recalculation of perfusion the previously calculated value of intrinsic thermal conductivity and in each recalculation of intrinsic thermal conductivity the previously calculated value of perfusion;

relating intrinsic thermal conductivity values for tissue with corresponding tissue water content values; and computing the water content of the volume of tissue as a function of said substantially unchanging value of intrinsic thermal conductivity and a substantially equivalent value of intrinsic thermal conductivity taken from the relationship of thermal conductivity values with tissue water content values.

4. A method for quantifying the water content of living tissue comprising the steps of:

placing a thermistor in contact with tissue at a site where water content is to be quantified;

energizing during a time interval the thermistor to elevate the temperature of the thermistor and heat tissue at the site above the baseline temperature of tissue at the site;

relating the rate at which heat is transferred in tissue with tissue water content; and quantifying the water content of tissue at the site as a function of the power supplied to the thermistor during the time interval, the rate at which heat from the thermistor is transferred in tissue at the site and the relationship established in said relating step.

5. A method for monitoring the water content of living tissue at a selected site comprising the steps of:

causing the temperature of tissue at the site to rise and fall cyclically;

producing a signal during each temperature cycle functionally related to the power used in said causing step and a thermal property of the tissue at the site, which thermal property varies as a function of tissue water content; and using a model of the relationship of the thermal property of tissue to tissue water content, computing the water content of tissue at the site during each temperature cycle as a function of the signal resulting from said signal producing step and the modeled relationship.

6. A method for monitoring the water content of living tissue comprising the steps of:

introducing into tissue an energizable thermistor adapted for thermal contact with tissue surrounding said thermistor;

energizing and deenergizing said thermistor cyclically to cause the temperature of the surrounding tissue to rise and fall cyclically;

producing a signal during each energizing and deenergizing cycle functionally related to the power used to energize said thermistor and the thermal conductivity of the surrounding tissue;

modeling the relationship of tissue water content and the thermal conductivity of tissue;

calculating the value of the intrinsic thermal conductivity of the surrounding tissue in a first time interval during each energizing and deenergizing cycle;

calculating perfusion in a subsequent time interval during each energizing and deenergizing cycle using the calculated value of intrinsic thermal conductivity;

recalculating intrinsic thermal conductivity in said first time interval using the calculated value of perfusion;

recalculating values for perfusion and intrinsic thermal conductivity, in alternating fashion, until the recalculated values of intrinsic thermal conductivity converge to a substantially unchanging value, using in each recalculation of perfusion the previously calculated value of intrinsic thermal conductivity and in each recalculation of intrinsic thermal conductivity the previously calculated value of perfusion; and computing the water content of the surrounding tissue during each energizing and deenergizing cycle as a function of said substantially unchanging value of intrinsic thermal conductivity and the relationship resulting from said modeling step.

7. A method for assessing water content of living tissue comprising the steps of:

supplying thermal energy to tissue to cause the temperature of tissue at a selected site to rise; and calculating a value indicative of tissue water content of tissue at the selected site as a function of the power used in said heating step and the temperature rise of tissue at the selected site, at least one of which is predetermined, and a value provided by a model relating tissue conductivity or tissue diffusivity to tissue water content.

8. A method for assessing the water content in living tissue at a site in the body comprising the steps of:

introducing a thermistor into contact with tissue at a site where water content is to be assessed;

energizing the thermistor to elevate the temperature of the thermistor above the baseline temperature of tissue at the site;

producing a signal as a function of the energy supplied to the thermistor in said energizing step and the rate at which heat from the thermistor is transferred in tissue at the site; and using a known relationship which correlates the rate at which heat is transferred in tissue with tissue water content and the signal resulting from said producing step, producing a signal indicative of the water content of tissue at the site.

9. A system for quantifying water content of living tissue comprising:

a thermistor for heating a volume of tissue;

means for energizing said thermistor to cause the temperature of the volume of tissue to rise;

means for relating tissue conductivity to tissue water content; and means communicating with said energizing means and said relating means for calculating tissue water content of said volume of tissue as a function of the power used to heat said thermistor and the temperature rise of said thermistor, at least one of which is controlled in a predetermined manner, and a water content value obtained from said relating means.

10. A system according to claim 9 wherein:

said energizing means comprises means for energizing said thermistor cyclically to cause the temperature of the volume of tissue to rise and fall cyclically;

said relating means comprises a look-up reference; and said calculating means comprises means for calculating the tissue water content of said volume of tissue in each energizing cycle as a function of the power used to heat said thermistor in each energizing cycle and the temperature rise of said thermistor in each energizing cycle, at least one of which is predetermined, and a water content value obtained from said look-up reference relating tissue conductivity to tissue water content.

11. A system for assessing water content in living tissue comprising:

thermistor means for thermally contacting tissue at a site where tissue water content is to be assessed;

means for energizing and deenergizing said thermistor means to cause the temperature of tissue at the site to rise and fall;

means for producing a signal during the energizing and deenergizing cycle as a function of the power used to energize said thermistor means and at least one thermal property of tissue at the site, which thermal property varies as a function of tissue water content;

means for modeling the relationship of tissue water content to the at least one thermal property of tissue; and means for assessing the water content of tissue at the site during the energizing and deenergizing cycle as a function of the signal resulting from said signal producing means and the relationship modeled by said modeling means.

12. A system according to claim 11 wherein:

said energizing means comprises means for cyclically energizing and deenergizing said thermistor means to cause the temperature of tissue at the site to rise and fall cyclically;

said signal producing means comprises means for producing during each energizing and deenergizing cycle a signal as a function of the power used to energize said thermistor means during each energizing and deenergizing cycle and at least one thermal property of tissue at the site; and said means for assessing tissue water content comprises means for assessing the water content of tissue at the site in each energizing and deenergizing cycle as a function of the signal resulting from said signal producing means in each energizing and deenergizing cycle and the relationship modeled by said modeling means.

13. A system according to claim 11 or 12 wherein said signal producing means comprises means for producing a signal as a function of the thermal conductivity of tissue at the site and the power used to energize said thermistor means.

14. A system according to claim 11 or 12 wherein said signal producing means comprises means for producing a signal as a function of the thermal diffusivity of tissue at the site and the power used to energize said thermistor.

15. A system according to claim 11 or 12 wherein said thermistor means comprises a probe adapted to be introduced invasively into tissue at a site where tissue water content is to be assessed and at least one thermistor mounted on said probe for contact with tissue at the site.

16. A system according to claim 11 or 12 wherein said thermistor means comprises a noninvasive probe adapted for thermal contact with the surface of tissue at a site where tissue water content is to be assessed and at least one thermistor mounted on said probe for contact with tissue at the site.

17. A system for monitoring water content in living tissue comprising:

a probe adapted for contact with the surface of tissue at a site where tissue water content is to be quantified;

a thermistor on said probe adapted for thermal contact with the tissue surface;

means for energizing and deenergizing said thermistor cyclically when said thermistor is in contact with the tissue surface to cause the temperature of tissue at the site to rise and fall cyclically;

means for producing a signal during each energizing and deenergizing cycle as a function of the power used to energize said thermistor;

means for correlating water content of tissue to tissue conductivity; and means for quantifying the water content of tissue at the site in each energizing and deenergizing cycle as a function of the signal produced by said producing means in each energizing and deenergizing cycle and the correlation established by said correlating means.

18. A system for assessing the water content of tissue comprising:

means for thermally energizing tissue at a selected site;

means for relating tissue water content to a thermal property of tissue, which thermal property of tissue varies as a function of tissue water content;

means indicative of the thermal response produced in tissue at the site, which thermal response is a function of said thermal property of tissue at the site; and means for indicating the water content of tissue at the site as a function of the relationship established by said relating means, the energy used to energize tissue at the site and the thermal response produced in the tissue at the site.

19. A system for assessing the water content of tissue comprising:

means for heating tissue to be assessed;

modeling means for relating tissue water content to an intrinsic thermal property of tissue which varies as a function of tissue water content;

means for producing a signal as a function of the power used by said heating means to heat the tissue to be assessed and the thermal response produced in the tissue to be assessed, which thermal response is a function of said intrinsic thermal property of the tissue to be assessed; and means communicating with said producing means and said modeling means for producing a signal indicative of the tissue water content of tissue to be assessed as a function of the signal produced by said producing means and the relationship established in said modeling means.

20. A system for assessing the water content of tissue comprising:

a thermistor adapted for thermal communication with tissue to be assessed;

control means for heating said thermistor and producing a signal functionally related to the power used to heat said thermistor and the temperature rise of said thermistor;

means for relating tissue thermal conductivity to tissue water content; and means communicating with said control means and said relating means for producing a signal indicative of the water content of tissue to be assessed as a function of the signal produced by said control means and the relationship established by said relating means.

21. A system for assessing the water content of tissue comprising:

a thermistor adapted for thermal communication with tissue to be assessed;

energizing means for heating said thermistor;

means for relating tissue thermal conductivity to tissue water content; and means for indicating of the water content of tissue to be assessed as a function of the relationship established by said relating means, the energy used to heat said thermistor and the temperature rise of said thermistor.

* * * * *

UNITED STATES PATENT AND TRADEMARK OFFICE
CERTIFICATE OF CORRECTION

PATENT NO.    : 6,488,677 B1                                              Page 1 of 1
DATED         : December 3, 2002
INVENTOR(S)   : Harry Frederick Bowman and Gregory T. Martin It is certified that error appears in the above-identified patent and that said Letters Patent is hereby corrected as shown below:

<u>Drawings,</u>
Sheet 1, Fig. 1, change the reference numeral for "Water Content Model" to -- 26 --.
Sheet 1, Fig. 1, change "Vg(t)" to --Vs(t) --; and
Sheet 6, Fig. 10, delete the reference numeral "22".

Signed and Sealed this

Twenty ninth Day of April, 2003

JAMES E. ROGAN
*Director of the United States Patent and Trademark Office*